(12) United States Patent
Kimura et al.

(10) Patent No.: US 6,182,519 B1
(45) Date of Patent: Feb. 6, 2001

(54) METHOD FOR QUALIFYING THE CYLINDER VALVE ON GAS CYLINDERS

(75) Inventors: Masao Kimura, Minato-machi; Kohei Tarutani, Tsukuba, both of (JP)

(73) Assignee: L'Air Liquide, Societe Anonyme pour l'Etude et l'Exploitation des Procedes Georges Claude, Paris (FR)

( * ) Notice: Under 35 U.S.C. 154(b), the term of this patent shall be extended for 0 days.

(21) Appl. No.: 09/268,685

(22) Filed: Mar. 16, 1999

(30) Foreign Application Priority Data

Mar. 17, 1998 (JP) .................................................. 10-067281

(51) Int. Cl.[7] ........................................................ B08B 1/00
(52) U.S. Cl. ............................................................ 73/865.9
(58) Field of Search .............................. 73/865.9, 865.5, 73/168; 15/300.1, 301, 316.1, 363, 382, 405–407; 137/238

(56) References Cited

U.S. PATENT DOCUMENTS 3,943,959 * 3/1976 Kirkland .
4,261,075 * 4/1981 Gruen .
4,461,651 * 7/1984 Hall .
4,653,525 * 3/1987 Young .
5,676,762 10/1997 Kimura et al. .
5,860,187 * 1/1999 Flaszynski et al. .

FOREIGN PATENT DOCUMENTS 7-134090   5/1995 (JP) .

OTHER PUBLICATIONS

Patent abstract of 07–134090, Not Dated.

* cited by examiner

Primary Examiner—Robert Raevis
(74) Attorney, Agent, or Firm—Burns, Doane, Swecker & Mathis, L.L.P

(57) ABSTRACT

Provided is a safe method for qualifying the cylinder valves on gas cylinders, which method can also clean the cylinder valve when necessary. Compressed gas residing in a gas cylinder is discharged through the flow path of a cylinder valve with the cylinder valve on the gas cylinder in an open position. During this process ultrasound vibrations from the generator are applied to the cylinder valve and the number of particles in the outflowing gas is counted by a detector. The cleanliness of the cylinder valve is evaluated based on the detected value of the number of particles provided by the detector. When the detected value exceeds a standard value, the application of ultrasound vibrations, counting of the number of particles, and evaluation of the cleanliness are repeated until the detected value reaches or falls below the standard value.

11 Claims, 2 Drawing Sheets

METHOD FOR QUALIFYING THE CYLINDER VALVE ON GAS CYLINDERS

BACKGROUND OF THE INVENTION

1. Field of the Invention

Figure 1:
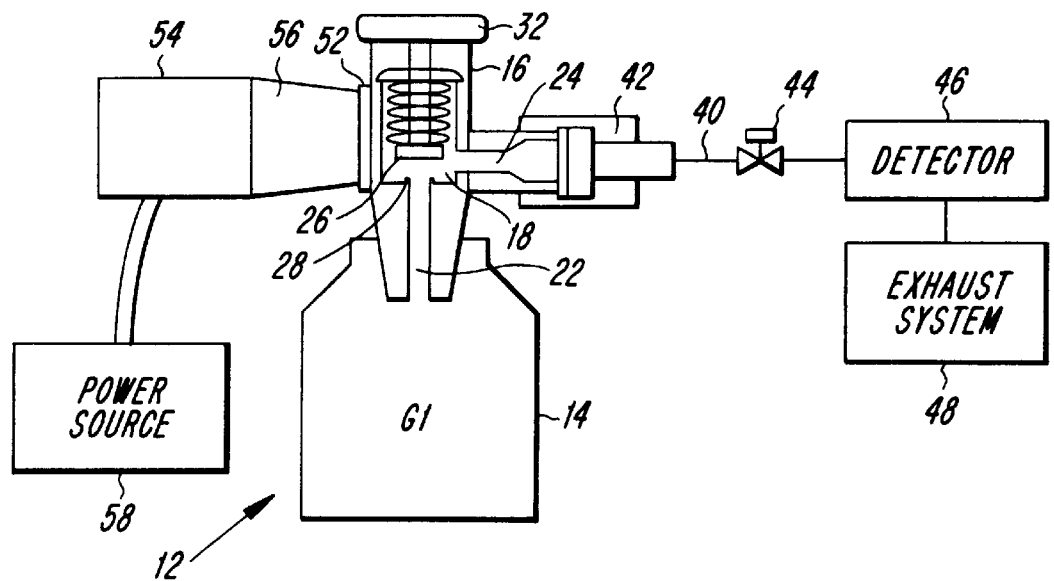

The present invention relates to a method for qualifying the cleanliness of the cylinder valve on a gas cylinder, which includes an optional cleaning of the cylinder valve if necessary. The main standard for qualifying cylinder valve cleanliness is based on the number of particles adhering to the interior wall of the flow path.

2. Description of the Related Art

Processes for fabricating semiconductor devices and electronic equipment require that the distribution system for the process gases used, for example, the reactive gases and carrier gases, be as clean as possible. The sources of contamination that can impair the cleanliness of such gas distribution systems are believed to be the gas itself, as acquired, the gas cylinders filled with and holding the gas, and atmospheric air that has become admixed during the filling process.

Japanese Patent Application Laid Open (Kokai or Unexamined) Number Hei 7-134090 (134,090/1995) discloses a method for qualifying (evaluating) and processing the cylinder body in view of the contamination by metal microparticles (particles) from the interior wall surface of the cylinder body of gas cylinders. In this method, the cleanliness of the cylinder body is evaluated by discharging the interior gas while applying ultrasound to the cylinder body and by analyzing the discharged gas.

However, the cylinder valve of a gas cylinder is considered to be a more significant source of gas distribution system contamination than either the gas as supplied or the cylinder body, because the cylinder valve is subjected to processes that result in the production of larger numbers of particles. For example, friction between the valve body and valve seat, corrosion of the components within the cylinder valve by corrosive gases, and reactions between air and highly reactive gases can all lead to contamination. Moreover, taking as an example the widely used 47-liter cylinder, the linear gas velocity within the cylinder valve can be 1,000 times or more than that within the cylinder when gas is supplied from the cylinder at a prescribed flowrate, which causes the gas flow-induced particle desorption probability to be much larger within the cylinder valve than within the cylinder.

In U.S. Pat. No. 5,676,762 there is disclosed a method for cleaning ultrahigh purity gas distribution systems (which include the cylinder valves of gas cylinders). This method cleans all the components within the flow path of a gas distribution network using a solvent as a cleaning fluid. This method is very useful for clearing the distribution systems for corrosive gases such as HBr, HCl, $NH_3$, and the like.

The deposition of large amounts of particles on the interior surfaces of the cylinder valves used with highly reactive gases such as $SiH_4$, $PH_4$, $B_2H_6$, and so forth has been observed. These particles are composed of the reaction products, such as $SiO_2$ and $P_4O_{10}$, resulting from the reaction of these highly reactive gases with air. These particles adhering on the interior surfaces of the cylinder valve debond during gas filling and gas removal and enter the gas flow, and in this manner contaminate the incoming or outgoing gas. Due to its use of a solvent as a cleaning fluid, the method of U.S. Pat. No. 5,676,762 is disadvantageous from a safety standpoint for the cleaning of cylinder valves which are used with highly reactive gases such as $SiH_4$, $PH_4$, $B_2H_6$, and so forth.

An object of the present invention therefore, is to provide a method that, by virtue of being different in its aspects from the prior art, is a very safe method for evaluating and qualifying the cleanliness of cylinder valves and in particular is optimal for application to the cylinder valves of gas cylinders for highly reactive gases.

An additional object of the present invention is to provide a qualification method in which, based on the results of the evaluation of the cleanliness of the cylinder valve, the cylinder valve can be cleaned subsequent thereto.

These and other objects of the present invention will become apparent upon a review of the following specification, the Figures of the Drawing, and the claims appended hereto.

SUMMARY OF THE INVENTION

In accordance with the foregoing objectives, the present invention provides a method for qualifying a cylinder valve on a gas cylinder, which comprises a discharge process in which compressed gas in a gas cylinder is discharged through the flow path of the cylinder valve with said cylinder valve on the gas cylinder in the open position, a detection process in which, during the aforesaid discharge process, the number of particles in the gas being discharged through the said flow path of the said cylinder valve is counted while vibrations are applied to the said cylinder valve, and an evaluation process in which the cleanliness of the said cylinder valve is evaluated based on the detected value for the number of particles that is provided by the aforesaid detection process.

In a second embodiment, the method for qualifying the cylinder valve on a gas cylinder comprises a feed/discharge process in which, while the cylinder valve on a gas cylinder is in the closed position, fluid is alternately fed into and discharged from the flow path of the said cylinder valve through the outlet of the said cylinder valve, a detection process in which, during the aforesaid feed/discharge process, the number of particles in the said fluid being discharged from the said outlet of the said cylinder valve is counted while vibrations are applied to the said cylinder valve, and an evaluation process in which the cleanliness of the said cylinder valve is evaluated based on the detected value for the number of particles that is provided by the aforesaid detection process.

A third embodiment of the present invention is characterized in that, when the detected value in the method of the first or second embodiments described above exceeds a standard value, the detection and evaluation processes are carried out repeatedly until the detected value is no greater than a standard value.

In a fourth embodiment of the present invention, when the detected value in the method of the first or second embodiments described above exceeds a standard value, a cleaning process is additionally provided after the evaluation process wherein this cleaning process comprises discharging compressed gas within the cylinder through the flow path of the open cylinder valve while applying vibrations to the cylinder valve.

A fifth embodiment of the present invention is characterized in that, when the detected value in the method of the first or second embodiments described above exceeds a standard value, a cleaning process is additionally provided after the evaluation process wherein the cleaning process comprises the application of vibrations to the cylinder valve while alternately feeding a fluid into and discharging said fluid from the flow path of the cylinder valve through the outlet of the cylinder valve while the cylinder valve is in closed position.

A sixth embodiment of the present invention is characterized by the additional provision in the methods according to any of the foregoing embodiments of a process for analyzing the metal in the aforesaid gas or fluid.

A seventh embodiment of the present invention is characterized in that the vibrations applied to the cylinder valve during the detection process in the methods according to any of the foregoing embodiments are induced by ultrasound.

An eighth embodiment of the present invention is characterized by application of the ultrasound in the method according to the seventh embodiment in the form of pulses with a width of from 1 millisecond to 10 seconds and an interval of from 100 milliseconds to 100 seconds.

In a ninth embodiment, the present invention is characterized in that the ultrasound in the methods according to the seventh or eighth embodiments is generated by a generator attached to the cylinder valve through a sound coupler and is communicated to the cylinder valve through this coupler A tenth embodiment of the present invention is characterized in that the ultrasound is generated in the methods according to the seventh or eight embodiments by a vibrator not in contact with the cylinder valve, and is communicated to the cylinder valve through the vibration of an air layer.

An eleventh embodiment of the present invention is characterized in that the gas cylinder in the methods according to any of the foregoing embodiments is intended to be filled with a gas selected from electronic industry gases, including $SiH_4$, $PH_4$, and $B_2H_6$.

BRIEF DESCRIPTION OF THE FIGURES OF DRAWING

FIG. 1 of the Drawing contains a schematic drawing depicting a method of the present invention for qualifying the cylinder valve of a gas cylinder.

Figure 2:
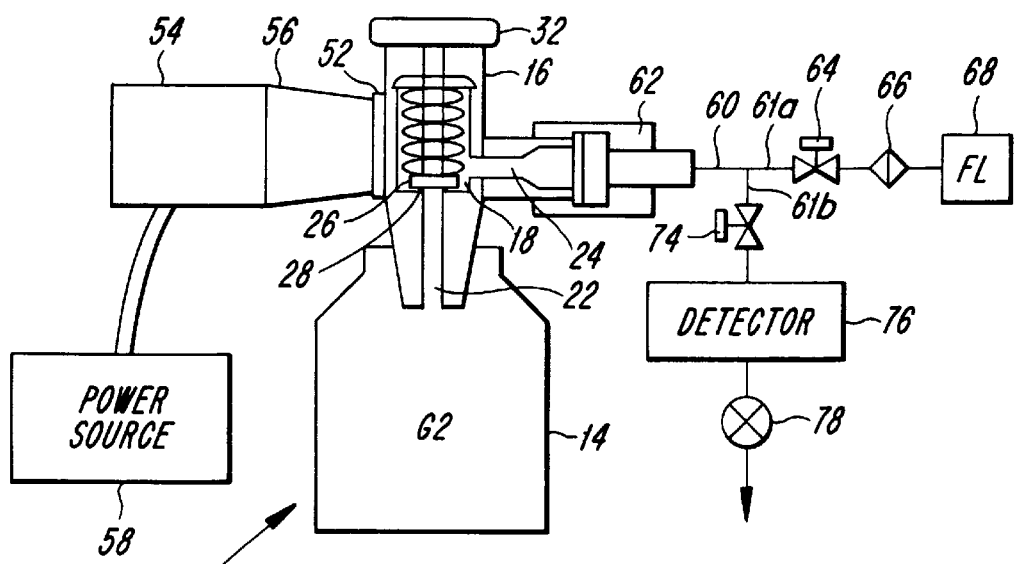

FIG. 2 of the Drawing contains a schematic drawing depicting a method of the present invention for qualifying the cylinder valve of a gas cylinder.

Figure 3:
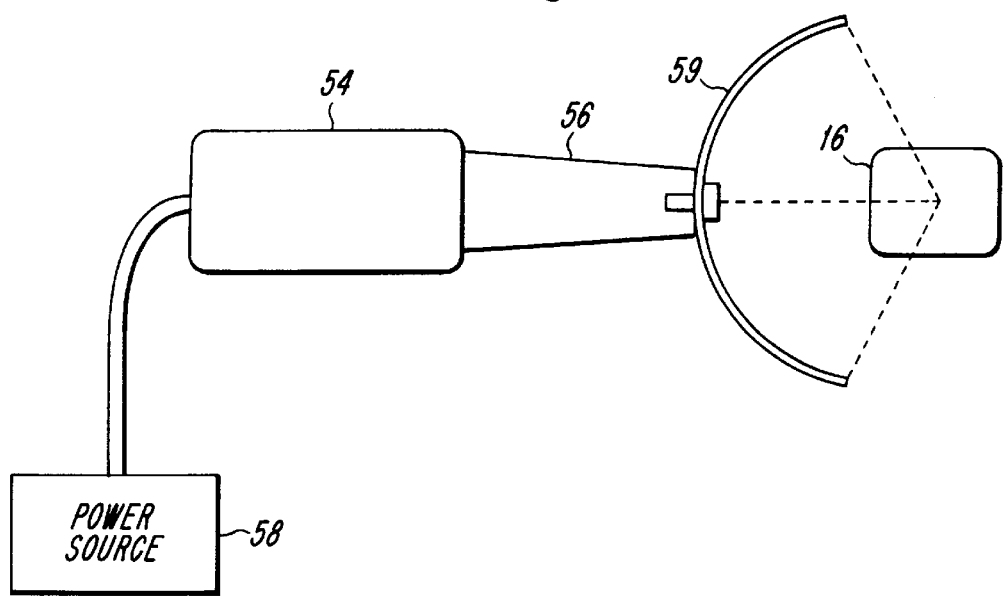

FIG. 3 of the Drawing contains a schematic drawing depicting an example of the application of ultrasound vibrations to the cylinder valve of a gas cylinder.

Figure 4:
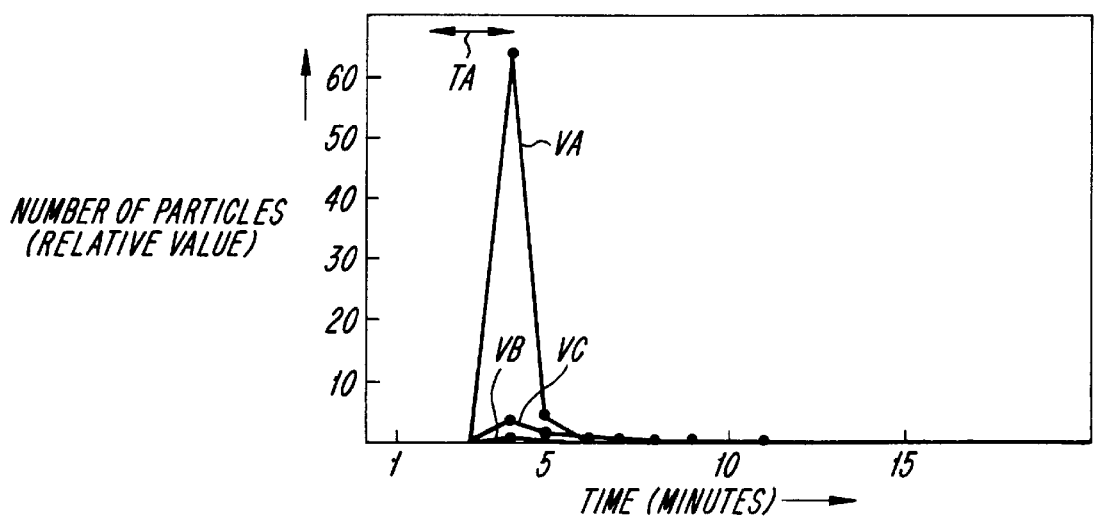

FIG. 4 contains a graph illustrating the experimental results from the qualification method depicted in FIG. 1 on 3 cylinder valves having different degrees of contamination.

In the Figures of the Drawing, the following reference numbers are used:

12 . . . gas cylinder
14 . . . cylinder valve
40 . . . detection line
46 . . . detector
48 . . . exhaust system
52 . . . sound coupler
54 . . . ultrasound generator
56 . . . horn
59 . . . concave sheet
60 . . . detection line
68 . . . fluid source
76 . . . detector
78 . . . suction pump

DETAILED DESCRIPTION OF THE PREFERRED EMBODIMENTS

In the discussions that follow, structural elements that have approximately the same function and structure are assigned the same reference number in the Figures of the Drawing, as noted above, and duplicate explanations are provided only when absolutely necessary.

Turning to the Figures of the Drawing, FIG. 1 contains a schematic drawing that depicts the execution of one embodiment of the method according to the present invention for qualifying the cylinder valve of gas cylinders. As shown in FIG. 1, the gas cylinder 12 is provided with a cylinder valve 16 of known type installed on the inlet/outlet of the cylinder body 14. There is formed within this valve 16 a flow path 18 that runs from the inlet 22 (inserted in the cylinder body 14) to the outlet 24 on the atmosphere side. Flow path 18 is opened and closed by the valve body 26, which is itself driven by the handle 32 and closes against or retreats from the valve seat 28.

The method for qualifying the cylinder valve 16 according to the embodiment under consideration can be run, for example, after the gas filled within the cylinder has been consumed, that is, after the gas cylinder 12 has been recovered. Prior to carrying out the subject qualifying method, with the cylinder valve 16 in its closed position, a detection line 40 is first connected to the outlet 24 of the cylinder valve 16 using connector 42. This detection line 40 is provided with a flowrate control valve 44 and with a detector 46 installed in the order given moving from the outlet 24 of the cylinder valve 16. This detector 46 is also connected to an exhaust system 48 that contains, for example, an intercept cylinder for the treatment of toxic gases.

The outer wall of the casing of the cylinder valve 16 is provided with an ultrasound generator 54 interfaced thereto by a sound coupler 52. A tacky substance, for example, a jelly, can be used as the sound coupler 52. The generator 54 is provided with a horn 56 for amplification of the sound wave vibrations, and the tip of this horn 56 is attached to the cylinder valve 16. The generator 54 is driven by a high-frequency power source 58 and can generate ultrasound in the frequency range from 20 kHz to 1 MHZ.

The gas present within the gas cylinder 12 must be under some elevated pressure in order to carry out the subject qualifying method. Thus, when the residual gas within the gas cylinder 12 does not reside at an adequately elevated pressure, a pressurized gas, for example, an inert gas, must be preliminarily injected into the gas cylinder 12.

The subject qualifying method can be run once the above-described preparations have been completed.

The embodiment under consideration commences with the execution of a discharge process, with the cylinder valve 16 in an open position. In this discharge process, a compressed gas G1 residing in the cylinder body 14 is discharged into detection line 40 through the flow path 18 of the cylinder valve 16.

A detection process is then carried out during the course of the discharge process. The generator 54 is started in this detection process and ultrasound vibrations are applied to the cylinder valve 16 through the horn 56 and coupler 52. This vibration causes debonding of the microparticles (particles) attached on the interior surfaces of the flow path 18 in the cylinder valve 16, and these debonded particles are subsequently discharged into the detection line 40 mixed with the discharged gas G1. The number of particles in the discharged gas is counted by the detector 46.

An evaluation process is then carried out based on the detected value afforded by the detection process. In this evaluation process, the cleanliness of the cylinder valve 16 is evaluated based on the detected value for the number of particles as counted by the detector 46, with a larger particle count being indicative of a lower cleanliness for the cylinder valve 16.

In order to avoid damaging the generator 54, the ultrasound is preferably generated in a pulse form by the generator 54. In specific terms, the ultrasound pulse width should be from 1 millisecond to 10 seconds, and is preferably from 10 milliseconds to 100 milliseconds while the interval should be from 100 milliseconds to 100 seconds, and is preferably from 1 second to 10 seconds. The ultrasound vibrations should be applied from 2 to 1,000 times, and preferably from 10 to 100 times, in a single evaluation process. As an example, when the discharging gas has a flowrate of 1 L/minute, the cleanliness of the cylinder valve 16 can be evaluated by application of the ultrasound vibration as described above about 60 times.

FIG. 2 contains a schematic drawing that depicts the execution of another embodiment of the method according to the present invention for qualifying the cylinder valve of gas cylinders. The method for qualifying the cylinder valve 16 according to this embodiment can be run, for example, on a gas cylinder 12 immediately after its interior has been filled with a gas G2, i.e., on a gas cylinder 12 just before its shipment.

Prior to the execution of the qualification method under consideration, with the cylinder valve 16 in its closed position, a detection line 60 is connected to the outlet 24 of the cylinder valve 16 using a connector 62. An ultrasound generator 54 is fixed, as in the embodiment depicted in FIG. 1, to the outer wall of the casing of the cylinder valve 16 through the interface of the sound coupler 52.

The detection line 60 is branched into a feed line 61a and a discharge line 61b. A fluid source 68 is connected to the feed line 61a across flowrate control valve 64 and check valve 66. The fluid FL, which is composed of a gas such as He or $N_2$, or a liquid such as water or alcohol, is fed into feed line 61a from the fluid source 68. The discharge line 61b is provided with a flowrate control valve 74, a detector 76, and a suction pump 78 in the order given moving from the outlet 24 of the cylinder valve 16.

The qualification method under consideration can be carried out once the above-described preparations have been completed.

In the case under consideration, a feed/discharge process is first run with the cylinder valve 16 in closed position. In this feed/discharge process, the fluid FL is alternately fed into and discharged from the flow path 18 of the cylinder valve 16 through the outlet 24 of the cylinder valve 16. During the feeding of the fluid FL, the valve 64 is opened and the valve 74 is closed and the fluid FL from the fluid source 68 is forced into the flow path 18 through the outlet 24 of the cylinder valve 16 as far as the valve body 26. During discharge of the fluid FL, the valve 64 is closed and the valve 74 is opened and pump 78 is engaged, resulting in a discharge of the fluid FL from flow path 18 into the discharge line 61b.

A detection process is also carried out while the subject feed/discharge process is underway. In this detection process, the generator 54 is started and ultrasound vibrations are applied to the cylinder valve 16 through horn 56 and coupler 52. These vibrations cause debonding of the microparticles (particles) adhering on the inner surface of the flow path 18 in cylinder valve 16, and these debonded particles are then discharged into the discharge line 61b mixed into the fluid FL. The number of particles in the fluid FL is counted by detector 76.

An evaluation process is then carried out based on the detected value afforded by the detection process. In this evaluation process, the cleanliness of the cylinder valve 16 is evaluated based on the detected value for the number of particles as counted by the detector 76, with a higher particle count being indicative of a lower cleanliness for the cylinder valve 16.

In this embodiment, the ultrasound is again preferably generated from the generator 54 in pulse form in order to avoid damaging the generator 54. The specific features desired for the ultrasound are the same as those described for the embodiment covered by FIG. 1. The ultrasound vibrations need not be applied during both the feed and discharge of the fluid FL, but may be applied during either period, or during the period in which switching between feed and discharge is being carried out.

The application of ultrasound in the embodiments illustrated in FIGS. 1 and 2 during discharge of the gas G1 or during feed and/or discharge of the fluid FL causes the particles adhering on the inner surfaces of the flow path 18 of the cylinder valve 16 to gradually debond, leading to a gradual decline in the amount of particles deposited on the inner surfaces. Thus, the application of the above-described detection process makes possible cleaning of the flow path 18 of the cylinder valve 16. For example, when the detected value for the number of particles as afforded by the initial detection and evaluation processes exceeds a specified standard value, the subject detection and evaluation processes may be repeatedly carried out until the detected value reaches or falls below the standard value. Through this means cleaning of the flow path 18 in the cylinder valve 16 can be continued until the specified cleanliness is achieved based on the standard value.

The flow path 18 and the cylinder valve 16 can also be cleaned in a simple cleaning process without counting the number of particles, i.e., without evaluating the cleanliness of the valve 16. In this particular case, the length of the cleaning process or the period of application of the ultrasound vibrations or the number of applications of the ultrasound vibrations can be determined based on the detected value for the number of particles afforded by the initial detection process and evaluation process.

The cleaning process can be easily carried out in a process based on the detection process—but excluding the particle count—which was carried out prior to the cleaning process. In this particular embodiment, the conditions in the detection process, for example, the flowrate of the gas or fluid, the vibration applied to the cylinder valve 16, and so forth, may differ from those in the cleaning process. In the embodiment shown in FIG. 2, the cleaning process can be carried out by a process based on the embodiment shown in FIG. 1, or the reverse sequence can be carried out. Specifically, after the evaluation process in the embodiment shown in FIG. 2 has been carried out, without using the fluid FL and with the cylinder valve 16 in open position, a cleaning process can be carried out by applying ultrasound vibrations while discharging the gas G2 from the gas cylinder 12.

Cylinder valve 16 should be replaced with a new valve when very poor cleanliness is confirmed for the cylinder valve 16 in the initial evaluation process, or when the particle count cannot be brought down to or below the standard value even by a cleaning operation.

As discussed above, the qualification methods described by the embodiments shown in FIGS. 1 and 2 are useful when highly reactive gases are filled within the cylinder 12. For example, when a highly reactive gas such as $SiH_4$, $PH_4$, or $B_2H_6$ is filled into the gas cylinder 12, the gas will react with air and reaction products such as $SiO_2$ or $P_4O_{10}$ will be deposited within the cylinder valve 16. The present invention, through the use of the gas fill or an inert fluid as the fluid flowing within the cylinder valve 16, can evaluate and clean the deposits within the cylinder valve 16 using very safe processes and without damaging the cylinder valve 16. In order to qualify the cleanliness of the cylinder valve 16 using another criterion, a process for analyzing the metal in the particles collected through the detection line 40 or 60 may additionally be carried out.

FIG. 3 contains a schematic drawing that shows a modified example for applying the ultrasound vibrations to the cylinder valve 16 on a gas cylinder 12. In this modified example the ultrasound generator 54 is provided with a concave sheet 59 that defines a circular arc and is fixed at the end of the horn 56. During use the generator 54 is positioned in such a manner that the cylinder valve 16 resides in the center of the circular arc described by the said concave sheet 59. In this configuration, the ultrasonic waves from the concave sheet 59 are transmitted in a converging fashion to the cylinder valve 16 through vibration of the air layer.

This modified example, because it does not require attachment of the generator 54 to the cylinder valve 16, offers the advantages of facilitating the preparatory work for qualification and avoids soiling the cylinder valve 16 by the jelly 52.

An important advantage to the ultrasound generator used in the embodiments in FIGS. 1, 2, and 3 is that it can vibrate the cylinder valve 16 without damaging the valve. However, the means for applying vibrations to the cylinder valve 16 is not limited to use of the ultrasound generator 54, and any of various means that can apply a prescribed mechanical impact to the cylinder valve 16 can be selected. For example, a means can be employed in which the cylinder valve 16 is struck by a hammer at a prescribed force.

EXAMPLE

The qualification method depicted in FIG. 1 was applied to cylinder valves VA, VB, and VC. These valves presented different degrees of cleanliness and were installed on 3 different recovered He gas cylinders. In this experiment, He gas residing in the gas cylinder was discharged through the cylinder valve at a pressure of 10 bar and a flowrate of 1 L/minute while pulses of ultrasound (frequency=27 kHz) were generated by generator 54 and applied to the cylinder valve. The ultrasound pulses had a width of 10 milliseconds and a frequency of 60 per minute. 100 pulses were used in each qualification process. A light-scattering particle counter was used as the detector 46 for counting the number of particles.

FIG. 4 graphically illustrate the results obtained in this experiment. The arrowheads TA show the time interval for application of the ultrasound pulses. As shown in FIG. 4, for each of the cylinder valves VA, VB, and VC the number of particles is seen to increase due to the application of the ultrasound pulses. In addition, a much larger quantity of particles was detected from cylinder valve VA than from cylinder valves VB and VC, which confirmed that cylinder valve VA required cleaning.

As has been discussed hereinabove, the method according to the present invention for qualifying the cleanliness of cylinder valves can evaluate and qualify cylinder valves by a very safe method, and in particular is applicable to the qualification of the cylinder valves of gas cylinders for highly reactive gases. Moreover, according to the method of the invention for qualifying the cleanliness of cylinder valves, the cylinder valve can be subjected to an immediately ensuing cleaning process based on the results of the evaluation of the cleanliness of the cylinder valve.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. Method for qualifying a cylinder valve on a gas cylinder, which comprises a discharge process in which compressed gas in a gas cylinder is discharged through a flow path of the cylinder valve with said cylinder valve on the gas cylinder in the open position, a detection process in which, during the aforesaid discharge process, the number of particles in the gas being discharged through the said flow path of the said cylinder valve is counted while vibrations are applied to the said cylinder valve, and an evaluation process in which the cleanliness of the said cylinder valve is evaluated based on the detected value for the number of particles that is provided by the aforesaid detection process.

2. The method of claim 1 for qualifying the cylinder valve of a gas cylinder, characterized in that, when the said detected value exceeds a standard value, the said detection and evaluation processes are carried out repeatedly until the detected value is no greater than the said standard value.

3. The method of claim 1 for qualifying the cylinder valve of a gas cylinder, characterized in that, when the said detected value exceeds a standard value, a cleaning process is additionally provided after the said evaluation process wherein said cleaning process comprises discharging compressed gas within the said cylinder through the flow path of the open cylinder valve while applying vibrations to the said cylinder valve.

4. The method of claim 1 for qualifying the cylinder valve of a gas cylinder, characterized in that, when the said detected value exceeds a standard value, a cleaning process is additionally provided after the said qualification process wherein said cleaning process comprises the application of vibrations to the cylinder valve while alternately feeding a fluid into and discharging said fluid from the flow path of the said cylinder valve through the outlet of the cylinder valve while the cylinder valve is in closed position.

5. The method of claim 1 for qualifying the cylinder valve of a gas cylinder, characterized in that said method additionally includes a process for analyzing metal in the aforesaid gas or fluid.

6. The method of claim 1 for qualifying the cylinder valve of a gas cylinder, characterized in that the vibrations applied to the said cylinder valve during the aforesaid detection process are induced by ultrasound.

7. The method of claim 6 for qualifying the cylinder valve of a gas cylinder, characterized by application of the ultrasound in the form of pulses with a width from 1 millisecond to 10 seconds and an interval from 100 milliseconds to 100 seconds.

8. The method of claim 6 for qualifying the cylinder valve of gas cylinder, characterized in that the ultrasound is generated by a generator attached to the said cylinder valve through a sound coupler and is communicated to the cylinder valve through said coupler.

9. The method of claim 6 for qualifying the cylinder valve of a gas cylinder, characterized in that the said ultrasound is generated by a vibrator not in contact with the said cylinder valve and is communicated to the cylinder valve through the vibration of an air layer.

10. The method of claim 1 for qualifying the cylinder valve of gas cylinders, characterized in that the gas cylinder is intended for filling with gas selected from electronic industry gases including $SiH_4$, $PH_4$, and $B_2H_6$.

11. The method of claim 2 for qualifying the cylinder valve of a gas cylinder, characterized in that said method additionally includes a process for analyzing metal in the aforesaid gas or fluid.

* * * * *